United States Patent [19]

Halpern et al.

[11] Patent Number: 5,107,831
[45] Date of Patent: Apr. 28, 1992

[54] VENTILATOR CONTROL SYSTEM USING SENSED INSPIRATORY FLOW RATE

[75] Inventors: Arieh S. Halpern, Riverside; Ioan T. Oltean, Corona, both of Calif.

[73] Assignee: Bear Medical Systems, Inc., Riverside, Calif.

[21] Appl. No.: 711,595

[22] Filed: Jun. 6, 1991

Related U.S. Application Data

[63] Continuation of Ser. No. 367,934, Jun. 19, 1989, abandoned.

[51] Int. Cl.$^5$ .......................... A61M 16/00; A62B 7/00
[52] U.S. Cl. .......................... 128/204.26; 128/204.21; 128/204.23
[58] Field of Search .......................... 128/204.21, 204.23, 128/204.26, 716, 719, 723, 202.22

[56] References Cited

U.S. PATENT DOCUMENTS

| | | | |
|---|---|---|---|
| 3,357,428 | 12/1967 | Carlson | 128/145.8 |
| 3,905,362 | 9/1975 | Eyrick et al. | 128/202.22 |
| 3,911,899 | 10/1975 | Hattes | 128/2 S |
| 3,967,619 | 7/1976 | Story et al. | 128/205.13 |
| 4,206,754 | 6/1980 | Cox et al. | 128/204.21 |
| 4,323,064 | 4/1982 | Hoenig et al. | 128/205.24 |
| 4,357,936 | 11/1982 | Ellestad et al. | 128/204.23 |
| 4,365,636 | 12/1982 | Barker | 128/716 |
| 4,414,982 | 11/1983 | Durkan | 128/716 |
| 4,457,303 | 7/1984 | Durkan | 128/204.24 |
| 4,519,387 | 5/1985 | Durkan et al. | 128/204.23 |
| 4,550,726 | 11/1985 | McEwen | 128/202.22 |
| 4,580,575 | 4/1986 | Birnbaum et al. | 128/671 |
| 4,602,644 | 7/1986 | DiBenedetto et al. | 128/207.18 |
| 4,838,257 | 6/1989 | Hatch | 128/204.21 |
| 4,883,051 | 11/1989 | Westenkow et al. | 128/204.21 |
| 4,932,402 | 6/1990 | Snook et al. | 128/204.23 |

OTHER PUBLICATIONS

"Ventilators", Dupuis, C. V. Mosby Co., @1986, p. 214.
Puritan-Bennett "7200 Series Option IO Pressure Support", Form AA-763 (Jun./1989), U.S.A., 76389.
Puritan-Bennett "7202 Display Accessory", Form AA-1143 (Dec./1989), U.S.A., 114387.
Puritan-Bennett 7200, "Series Microprocessor Ventilator", Form AA-214 (Aug./1988), U.S.A., 21488.
Puritan-Bennett 7200a, "Option #30/40 Respiratory Mechanics", Form AA-985, (Jan./1987), U.S.A., 98587.
Puritan-Bennett 7200a, "Enter the Expanding World of the 7200a", Form AA-992, (Sep./1988), U.S.A., 99288.
Puritan-Bennett 7200a, "Option #20 DC 1", Form AA-991 (Dec./1987), U.S.A., 99187.
Ventilators: Theory and Clinical Application, Dupuis, The C.V. Mosby Co., @1986, p. 19, and 291-311.

Primary Examiner—Edgar S. Burr
Assistant Examiner—K. L. Asher
Attorney, Agent, or Firm—Klein & Szekeres

[57] ABSTRACT

A ventilator control system is responsive to a flow rate signal from a flow rate sensor that senses the flow rate of gas to a ventilated patient. The ventilator control system provides an episode signal to a ventilator to actuate the ventilator to provide an assisted breath. The ventilator control system has an interactive control panel for providing an operator selectable duration signal scaled to define a selected time interval between breaths. An operator also selects a flow rate threshold signal scale to define the flow rate that must be exceeded to qualify a breath from a patient as a valid breath. Episode signal circuitry responds to the flow rate signal, the flow-rate threshold signal, and the duration signal to generate an episode signal in response to the flow rate signal failing to exceed the flow rate threshold signal within the selected time interval.

18 Claims, 7 Drawing Sheets

| VENTILATOR RATE, BPM<br>RATE INTERVAL TIME<br>(SECONDS) | 2<br>30 | 3<br>20 | 4<br>15 | 5<br>12 | 6<br>10 | 7<br>8.5 | 8<br>7.5 | 9<br>6.6 | 10<br>6 | 11<br>5.4 |
|---|---|---|---|---|---|---|---|---|---|---|
| 5 | ---------------------------------- | | | | | | | | | |
| 6 | ------------------------------ | | | | | | | | | |
| 7 | -------------------------- | | | | | | | | | |
| 8 | -------------------- | | | | | | | | | |
| 9 | ------------------ | | | | | | | | | |
| 10 | ---------------- | | | | | | | | | |
| 11 | -------------- | | | | | | | | | |
| 12 | -------------- | | | | | | | | | |
| 13 | -------------- | | | | | | | | | |
| 14 | ---------- | | | | | | | | | |
| 15 | ---------- | | | | | | | | | |
| 16 | ---------- | | | | | | | | | |
| 17 | ---------- | | | | | | | | | |
| 18 | ---------- | | | | | | | | | |
| 19 | ------ | | | | | | | | | |
| 20 | ------ | | | | | | | | | |
| 21 | ------ | | | | | | | | | |
| 22 | ------ | | | | | | | | | |
| 23 | ------ | | | | | | | | | |
| 24 | ------ | | | | | | | | | |
| 25 | ------ | | | | | | | | | |

Left axis: DURATION CONTROL SETTING, 42

VENTILATOR CONTROL SYSTEM USING SENSED INSPIRATORY FLOW RATE

CROSS-REFERENCE TO RELATED APPLICATION

This Application is a Continuation of co-pending application Ser. No. 07/367,934, filed Jun. 19, 1989, now abandoned.

Reference is made to microfiche Appendix A, submitted herewith and incorporated herein, consisting of one microfiche of twenty-four frames.

BACKGROUND OF THE INVENTION

1. Field of the Invention

This invention generally relates to the field of medical equipment for respiratory therapy and more specifically to the field of equipment for monitoring the breathing characteristics of a human patient who is breathing with the assistance of a ventilator.

Clinical treatment of a ventilated patient often calls for monitoring a patient's breathing to detect an interruption or an irregularity in the breathing pattern, for triggering a ventilator to initiate assisted breathing, and for interrupting the assisted breathing periodically to wean the patient off of the assisted breathing regime, thereby restoring the patient's ability to breath independently.

2. Prior Art

Monitor systems for the detection of apnea, the medical term for interruption or cessation of normal breathing in a patient are known. For example U.S. Pat. No. 4,519,387 to Durkan et al discloses a control circuit operating a valve to supply respiratory gas to a person if the person's breath does not occur within a predetermined, yet selectively variable, interval. To detect a cessation of breath, earlier systems used a variety of techniques, including measuring the impedance through the patient, which varies with patient respiration, as in U.S Pat. No. 4,580,575 to Birnbaum.

U.S. Pat. No. 3,911,899 to Hatties teaches the use of an electromagnetic sensor comprising a transmitter and a receiver attached to a patient,s chest to detect breathing. The sensor generates a signal in response to the expansion and contraction of the patient's chest. The signals produced are detected and filtered to determine if a breath has occurred. The signals produced by the sensor are influenced by any motion of the chest, even motion not related to breathing. An adjustable timer is provided for the detection of an apnea episode. A flow rate signal is not compared with an adjustable flow-rate signal level to determine if a breath is a valid breath. An output signal is not provided to control a ventilator.

U.S. Pat. No. 4,365,636 to Barker teaches the measurement of respiration activity as a signal voltage obtained from sensors attached directly to the body. The signal is therefore, a measure of change of body position or volume as a function of time. The signal measured is scaled and sampled at a fixed sample rate of eight or more cycles per breath. The amplitude of the samples is processed to determine the slopes of the waveform at points on the waveform, the slope values being stored. The slope values thus calculated characterize the movement of the part of the patient's anatomy to which the sensor is affixed.

U.S. Pat. No. 4,414,982 to Durkan shows a pressure sensor for the detection of inspiration by sensing a negative pressure of as little as 0.5 millimeters of water.

None of the above references teaches, discloses or suggests a ventilator control system that senses inspiratory flow rate to determine if the sensed flow rate signal exceeds the amplitude of an operator selected threshold to qualify a patient's breath as a valid breath, and that allows the operator to select and adjust the duration within which a valid breath must occur to avoid signaling the ventilator to provide one or more mandatory breathing cycles.

The prior art systems have not provided a ventilator control system that permits an operator to selectively adjust an inspiratory flow rate threshold for the patient being monitored, which threshold, if not exceeded within a selectively adjustable interval, results in a triggering episode that automatically actuates a ventilator to deliver a selected number of breaths.

SUMMARY OF INVENTION

It is an object of the invention to provide a ventilator control system that monitors a flow rate signal from a flow rate sensor that senses the inspiratory flow rate of a patient, and that generates a triggering or "episode" signal in response to the flow rate signal amplitude failing to exceed a predetermined, operator-adjusted threshold within a predetermined (and adjustable) period.

It is a second object of the invention to initiate a predetermined number of cycle commands to a ventilator at an operator-selected interval in response to an inspiratory episode. The ventilator is actuated to provide breathing assistance to the patient in response to each episode signal, while an alarm is provided to the operator in the form of an audible or visible signal or both.

It is a third object of the invention ventilator control system to count and store the number of episodes that have occurred within a predetermined past interval, such as the last hour, and to display the count to the operator.

The invention provides a ventilator control system that constantly monitors a patient,s inspiratory flow rate signal and only triggers a ventilator to provide a mandatory breath in response to the patient's inspiratory flow rate failing to exceed a predetermined flow-rate threshold within an operator selected interval.

PREFERRED EMBODIMENT

Referring now to the drawings, a preferred embodiment of the present invention is described in detail.

Figure 1:
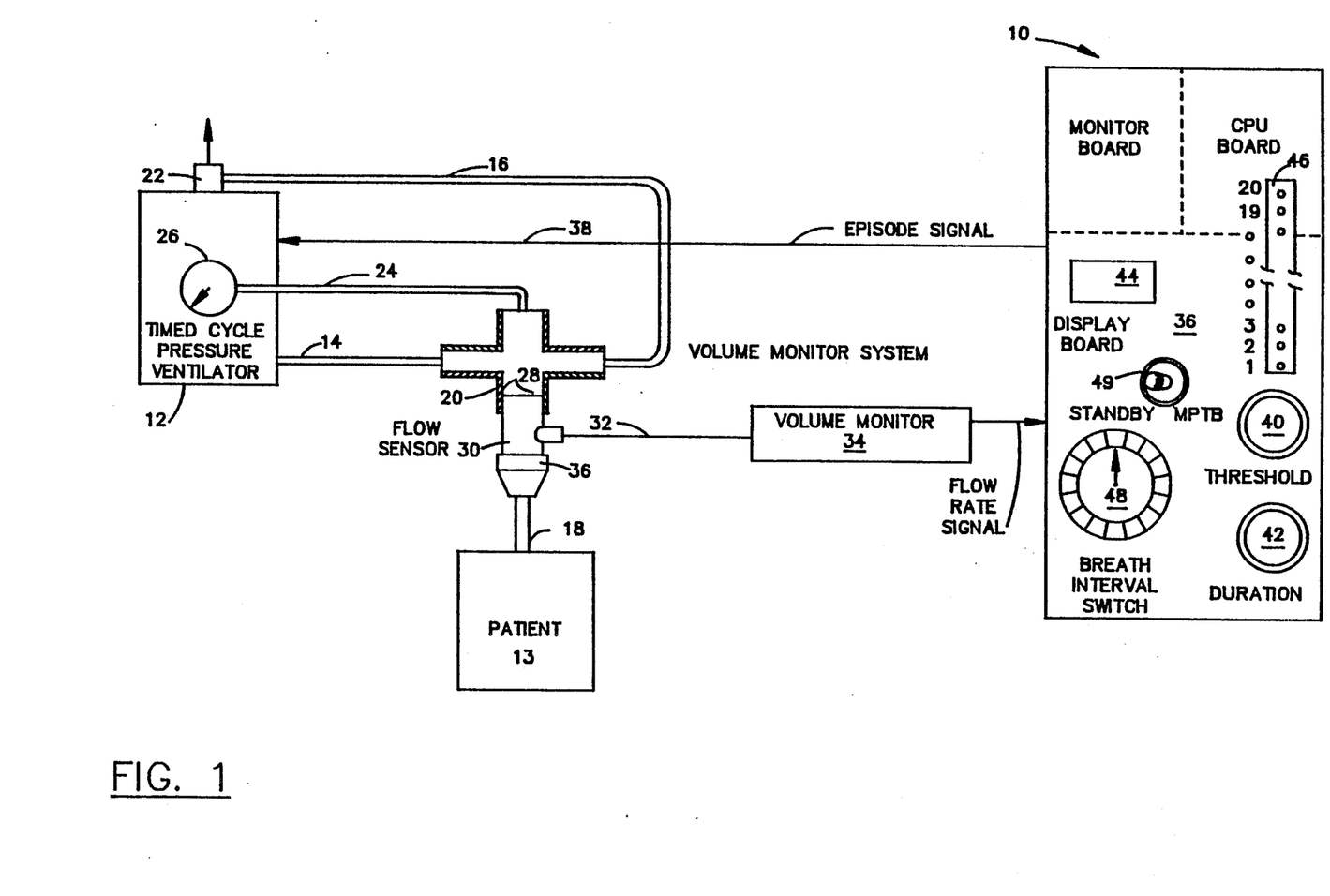
FIG. 1 is a block diagram showing the ventilator control system in accordance with a preferred embodiment of the invention in use with a pediatric ventilator.

FIG. 1 shows the ventilator control device 10 in use with a ventilator 12. A block 13 represents a patient who is breathing with the assistance of the ventilator 12. The ventilator 12 is of the constant-flow, time-cycled, pressure-limited type that is commonly used to ventilate pediatric patients. An example is the BEAR CUB[R] ventilator, manufactured by Bear Medical Systems, Inc., of Riverside, Calif. The ventilator 12 is connected to the patient 13 by a patient circuit comprising an inspiratory line 14, an expiratory line 16, and a patient connection tube 18, all connected by a patient connector 20, of a type well-known in the art.

In the normal, time-cycled ventilation mode, a stream of gas (typically air or oxygen-enriched air) is delivered from the ventilator 12 to the connector 20 via the inspiratory line 14. The patient draws from this gas stream through the patient connection tube 18 during inhalation, and returns exhaled gases to the connector 20 through the patient connector tube 18 during exhalation. The gas stream, periodically supplemented by the exhalation flow, is returned from the connector 20 back to the ventilator 12 by the expiratory line 16. The expiratory line 16 terminates in an exhalation valve 22 that is automatically operated by the ventilator to close during inhalation and open during exhalation.

The ventilator also includes a proximal pressure line 24 that leads from the patient connector 20 to a pressure transducer (not shown) in the ventilator. The pressure transducer measures the proximal pressure of the connector 20 to determine if the proximal pressure limit set on the ventilator by the clinician has been reached or exceeded The measured proximal pressure is advantageously displayed on a gauge 26 or a digital display (not shown).

As shown in FIG. 1, the patient connector 20 has a patient port 28, in which is installed a high-sensitivity flow sensor 30. The flow sensor 30 is preferably of the hot-wire type, with a capability of distinguishing between expiratory and inspiratory flows. Such a flow sensor is disclosed in U.S. Pat. No. 4,363,238, the disclosure of which is incorporated herein by reference.

The flow sensor 30 generates a flow rate-indicative output signal that is fed, via a signal cable 32, into a volume monitor 34, as will be described below. The proximal side (from the patient) of the flow sensor 30 is connected to the patient connection tube 18 by means of a tube adapter 36.

The volume monitor 34 is of a type, well-known in the art, that is capable of receiving and processing the output signal of the flow sensor 30 to produce a measurement of the patient's tidal volume. A suitable volume monitor is the BEAR[R] NVM-1 Neonatal Volume Monitor, marketed by Bear Medical Systems, Inc. of Riverside, Calif. This particular volume monitor is specifically designed for use with a flow sensor of the type described in U.S. Pat. No. 4,363,238, discussed above.

The volume monitor 34 contains microprocessor circuitry that receives the flow rate signal from the flow sensor 30 and processes it to calculate the values of various respiratory parameters, and to provide a visual display of these values.

Among these calculated parameters is the calculated tidal volume. Moreover, since the flow sensor 30 is bi-directional (i.e., capable of distinguishing between inspiratory and expiratory flow), the volume monitor 34 can indicate the total inhaled and exhaled tidal volumes by integrating the respective inhaled and exhaled flow rate signals over the total time of inspiration and expiration, respectively.

In addition, the volume monitor 34 processes the flow rate signals to provide an indication of the patient's breath rate.

The volume monitor 34 also generates an analog output signal indicative of flow rate, that is fed into the ventilator control device 10 for display on a display board 36.

FIG. 1 shows the ventilator control device 10 coupled to the ventilator 12 by a ventilator actuation line 38. The control device 10 provides an episode signal to the ventilator 12 to actuate the ventilator to provide an assisted breath or breaths. The display board 36 represents an interactive control panel for providing an operator-selectable duration signal scaled to define the selected maximum time interval between valid spontaneous breaths, and for providing an operator selectable flow rate threshold signal scaled to define the flow rate that must be exceeded to qualify a breathing response as a valid breath.

A threshold adjustment control 40 is used by the operator to select the desired threshold flow rate. A duration adjustment control 42 is used to select the episode-defining time interval between valid breaths. The threshold adjustment control 40 and the duration adjustment control 42 may be potentiometric controls manipulated by knobs on the display board 36.

The display board 36 includes an episode counter display 44 comprised of a pair of seven segment LED numerical indicators for displaying the number of episodes that have occurred in the last hour or in the hour preceding the last hour, at the operator's election. The display board 36 may also include an LED bar graph 46 of plural linearly-arrayed LEDs, (preferably about 20), for displaying the amplitude of the flow rate signal in real time as the signal is monitored. Display driver circuitry (described below) in the display board 36 provides enhanced illumination of one of the bar graph LEDs to show the value of the threshold signal that the operator has selected. The LED representing the selected threshold is brighter than the LEDs driven by the flow rate signal, as the latter rises and falls in response to the patient,s breathing.

A breath count and interval switch 48, preferably a rotary switch, is actuable by the operator to select both the number of breaths to be delivered to the patient in response to a detected episode, and the time interval between the breaths to be delivered. The switch is typically a 16 position BCD switch capable of providing 16 binary coded decimal values to a computer 50 (FIG. 2) to indicate what breath number and interval are selected.

The ventilator control device 10 is intended for use with a compatible ventilator capable of communicating with the ventilator control system. A typical ventilator such as the BEAR CUB ventilator has a CPAP (continuous positive airway pressure) mode which operates to maintain a continuous positive level of proximal pressure in the patient. This mode tends to keep the patient's lungs partially inflated at all times. If triggered by the ventilator control device, the ventilator delivers one to four breaths to the patient, depending on the position of the breath count and interval switch 48. The ventilator also has an IMV (Intermittent Mandatory Ventilation) mode in which the ventilator will only deliver one breath when triggered. To be fully compatible with the control device 10, the ventilator 12 requires the addition of actuation circuitry (described below) that triggers the ventilator in response to the episode signal received from the actuation line 38.

The ventilator control device is capable of providing multiple breaths from the ventilator when the ventilator control device is operating in the MPTB (Mandatory Patient Triggered Breath) mode as designated by the position of a mode switch 49 on the panel 36, and the ventilator is in the CPAP mode. The number of breaths and the interval between them is determined by the position of the breath count and interval switch 48.

With the mode switch 49 in the MPTB mode and the ventilator in the IMV mode, only one breath is delivered to the patient each time the ventilator control system generates an episode signal, regardless of the setting of the breath count and interval switch 48.

Figure 2:
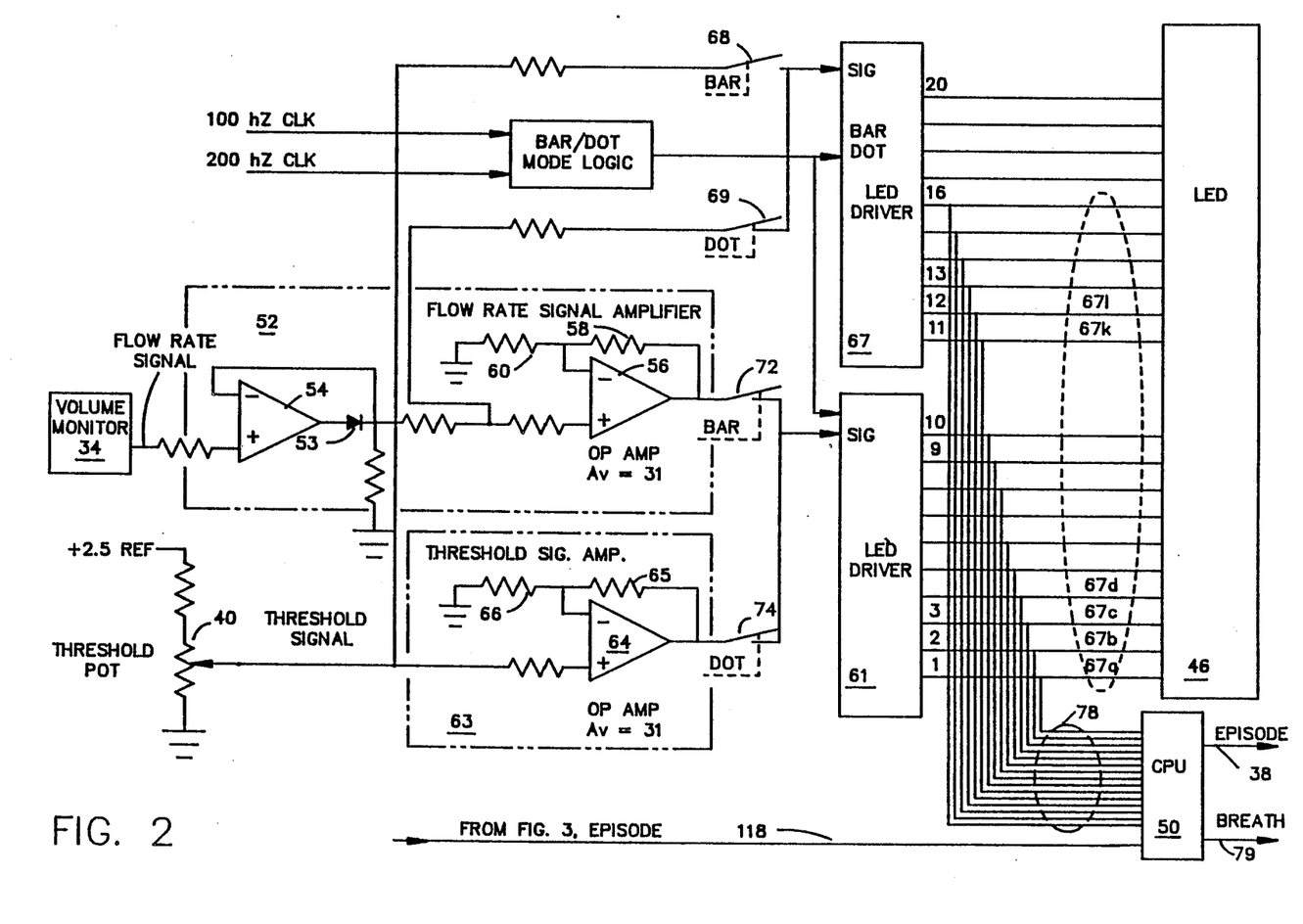
FIGS. 2 and 3 are schematic diagrams of the episode signal circuitry for generating and sending an episode signal to the ventilator.
Figure 3:
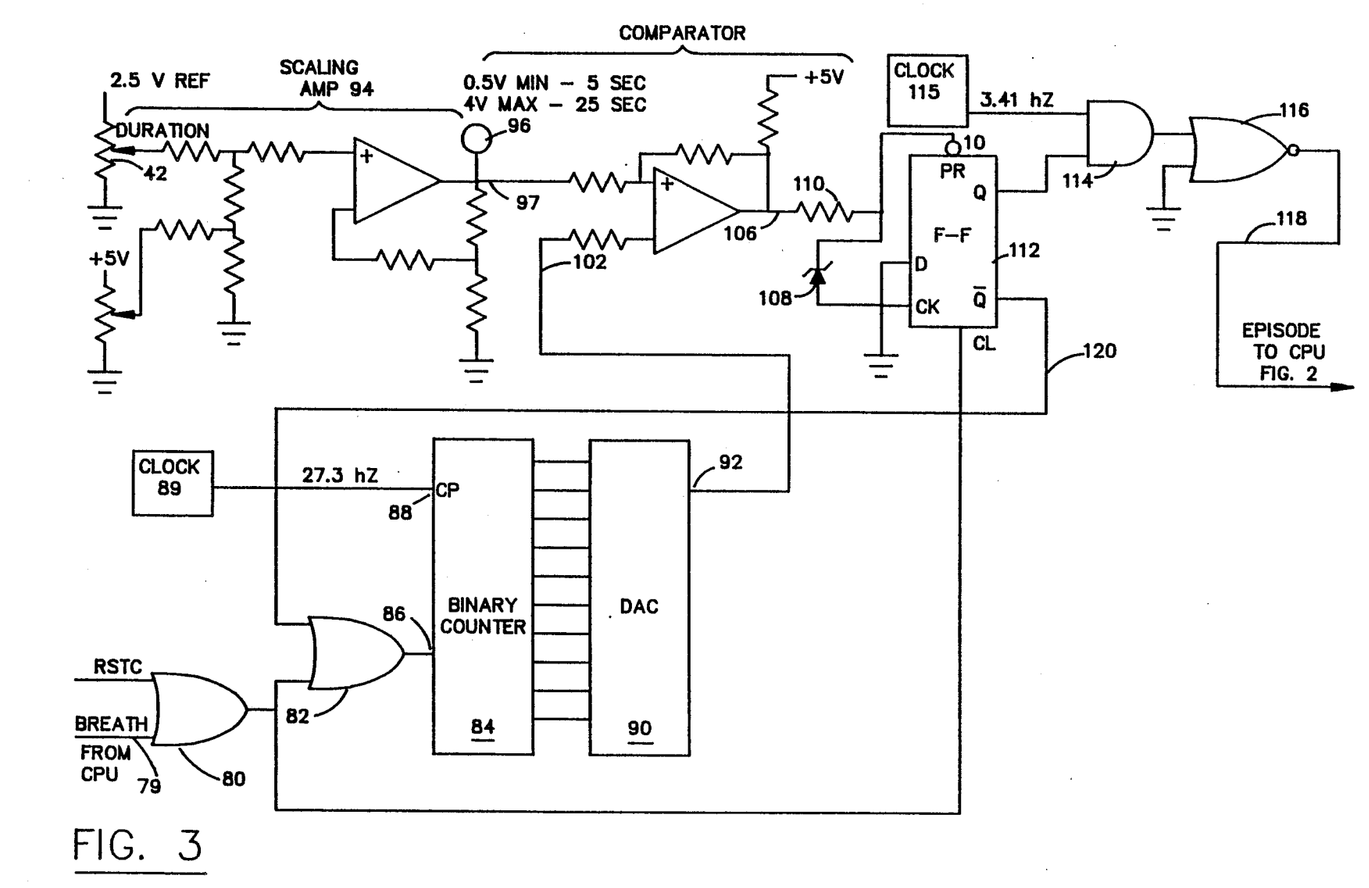
Figure 4:
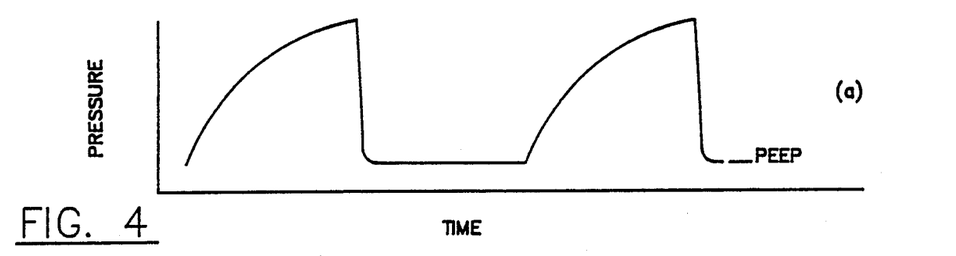
FIG. 4, waveform (a), is a graph of the pressure curve of a timed-cycle pressure limited ventilator, showing inspiratory flow.

FIGS. 2 and 3 together comprise a simplified schematic diagram of an episode signal generator that is responsive to the flow rate signal from the volume monitor 34 and to the flow rate threshold signal from the threshold adjustment control 40, for providing a zero level episode signal each time the flow rate signal amplitude exceeds the flow rate threshold signal level within the duration time set, as in normal breath cycles.

Referring first to FIG. 2, a computer 50 receives the flow rate signal and the flow rate threshold signal, and generates a breath indicative signal each time the flow rate signal amplitude exceeds the flow rate threshold level.

A flow rate rectifier amplifier 52 receives the flow rate signal directly from the volume monitor 34. A diode 53 on the output of a first op-amp 54 clips the negative swing of the flow rate signal and permits the output of the non-inverting voltage to follow only positive signals or signals that are more positive than the potential at ground.

The flow rate signal amplifier also comprises a non-inverting voltage amplifier using a second op-amp 56. The voltage gain of the non-inverting voltage amplifier is established by the ratio of first and second gain resistors 58 and 60 respectively. A voltage gain of 31 was used and found to be acceptable for a preferred embodiment of the invention using logarithmic type first and second LED drivers 61 and 67 respectively.

Amplification is provided for the signal inputs to the LED drivers 61 and 67 because of the wide dynamic range of the signals that are processed. Flow rate signals during marginal breathing may drop to levels as low as approximately 7 millivolts.

A threshold signal amplifier 63 amplifies the threshold signal by means of a non-inverting voltage amplifier using a third op amp 64 having a preferred voltage gain of 31, obtained by a pair of gain resistors 65 and 66. The voltage gain of 31 is chosen because the analog signal into the LED drivers is converted directly to a binary output by the LED drivers 61 and 67 in accordance with a logarithmic relationship by the drivers.

Each successively higher value LED weighted flow rate signal line 67a, 67b, 67c is grounded by its driver as the signal increases in value by a factor of 1.41 above that required to select the previous LED drive line. As the signal falls in amplitude, the signal must drop by a factor of 0.707 as each successive weighted flow rate signal line is allowed to go to a high logic level. The least significant weighted flow rate signal line 67k of the second LED driver 67 is scaled to require a signal that is 31 times greater in magnitude than the signal value for the least significant weighted flow rate signal line 67a of the first LED driver 61.

The second LED driver 67 is coupled to receive the flow rate signal and the threshold signal at alternate times by means of first and second analog switches 68 and 69 respectively. The first LED driver 61 receives the amplified flow rate signal and the amplified threshold signal at alternate times by means of third and fourth analog switches 72 and 74. The LED driver devices may be LM3915 devices from National Semiconductor, of Santa Clara, Calif.

The mode control of the LED drivers 61 and 67 is driven by a clocked logic circuit to switch the mode of the drivers from a dot mode to a bar mode. The flow rate and amplified flow rate signals are used to drive the drivers 61 and 67 in the bar mode, and the threshold signal and the amplified threshold signals are used to drive the drivers in the dot mode.

In the bar mode, the respective LED drivers 61 and 67 decode the magnitude of the flow rate signal into the respective "SIG" input and apply a ground to all of the LED weighted flow rate signal lines of increasing value that characterize the value of the flow rate signal. In the dot mode, only one weighted threshold signal line is grounded, and that line corresponds to the value of the threshold signal fed into the respective "SIG" input. The brightness of the LED displaying the amplitude of the threshold signal remains visible as the length of the bar exceeds the threshold signal amplitude because the LED is pulsed on for a longer duty cycle ratio.

The computer 50 uses a conventional CMOS version of the Z80 microprocessor to process the information obtained from the weighted flow rate signals and the weighted threshold signals. The information is read from a pair of busses (not shown) that lead from the first and second LED drivers 61 and 67, respectively, to the LED display 46. The information from the weighted threshold signal lines and the weighted flow rate signal lines is fed directly into a microcomputer input bus 78 by means of conventional programmable interface adapters (not shown) or equivalent means, as is well known in the art. The computer input bus 78 may typically be 16 bits, but, in any case, the bus 78 must be made wide enough to sample all of the weighted flow rate signals and weighted threshold signals required for resolution of the problem. When the computer 50 detects that the flow rate is higher than the threshold, the computer generates a breath-indicative signal on a breath signal line 79.

Referring now to FIG. 3, the breath indicative signal from the computer 50 is coupled to an input of a first OR gate 80. The second input to the OR gate 80 is a counter reset signal RSTC. The RSTC signal is normally in the low state, or false state. The output of the OR gate 80 goes high driving the output of a second OR gate 82 from a high to a low state, thereby resetting the outputs from a binary counter 84 to the zero or low state. The sequence of these events occurs each time the weighted flow rate signal into the computer 50 exceeds the weighted threshold signal.

Figure 5:
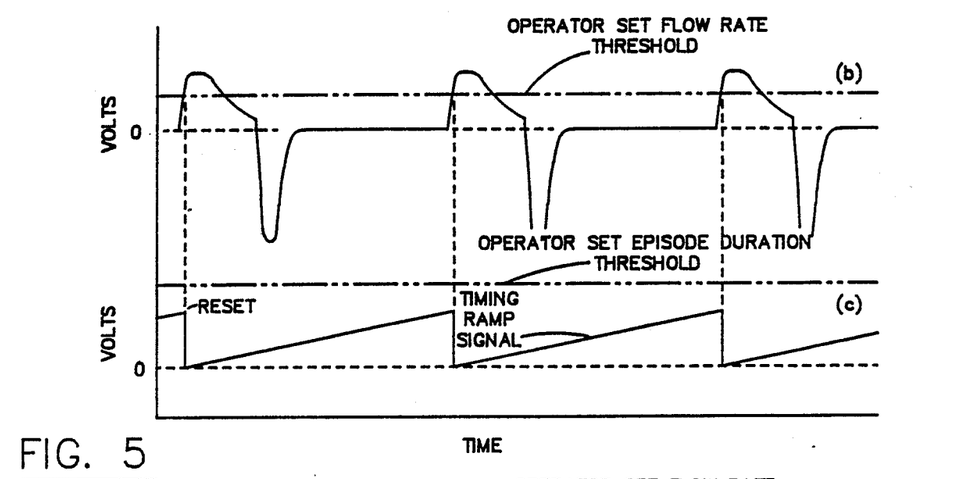
FIG. 5 shows waveform (b), a graph of the flow rate signal during normal breathing, and waveform (c) a graph of an associated timing ramp signal.

In FIG. 5, waveform (b) shows the shape of the flow rate signal during normal breathing. The operator selected threshold is penetrated on each successive cycle. Waveform (c) represents a timing ramp signal that is reset shortly after the flow rate signal is shown penetrating the threshold level superimposed on the graph above the timing ramp signal.

Referring again to FIG. 3, the reset signal to the binary counter 84 from the output of OR gate 82 is controlled by the computer 50 to be a short term event. After removal of the 84 again begins to advance its count in response to a 27.3 Hz clock signal fed into a clock signal input terminal terminal 88 from a first clock generator 89. The outputs of the counter 84, which may be a typical CMOS CD4040 device, advance in a conventional binary format. The outputs are received by a digital-to-analog converter (DAC) 90 which converts the count on the counter outputs to a voltage at an output terminal 92. The DAC may typically be an AD7533 device from Analog Devices of Norwood, Mass.

Figure 6:
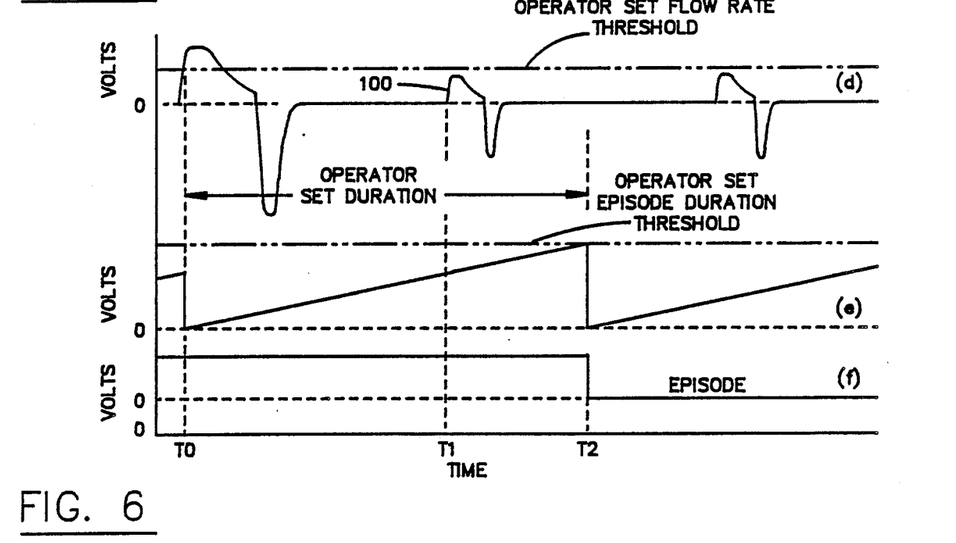
FIG. 6 shows waveform (d), a graph of the flow rate signal during abnormal breathing, waveform (e), an associated timing ramp signal, and waveform (f), a resulting episode signal.

The output of the DAC 90 at the output terminal 92 is represented by the timing ramp signal of waveform (c) in FIG. 5 and by waveform (e) in FIG. 6. It should be understood that the ramp signal increases in amplitude as a staircase and not as a straight incline as depicted in FIGS. 5 and 6.

Referring again to FIG. 3, the duration control 42 is excited by a 2.5 Vdc reference supply. The operator rotates the knob on the face of the control panel to an etch mark (not shown) on the face of the instrument designating the maximum time desired for the episode time interval. The duration signal thus selected is scaled by a scaling amplifier network 94 to a scaled duration signal level at a terminal 96. The amplifier is a non-inverting scaling amplifier. The signal level at the terminal 96 drives a first input 97 of a comparator 98, while the timing ramp signal drives a second input 102 to the comparator 98. The comparator may be a typical LM393 device.

FIG. 6 shows the sequence of waveforms that follow a decrease in a patient's inspiratory flow rate to a point at which the flow rate signals to the computer 50 cease to reach the level of the threshold. A flow rate cycle 100 in waveform (d) fails to exceed the flow-rate threshold level. The timing ramp waveform (e) is not reset at time T1 because the computer 50 failed to provide a breath indicative signal to the first OR gate 80, as discussed above.

The timing ramp continues to rise until it reaches a timing threshold level at time T2. This event occurs at inputs 97 and 102 of the comparator 98 in FIG. 3. The output of the comparator at its output terminal 106 transitions from a high level to a low level, as shown by waveform (f) in FIG. 6. A zener diode 108 and a resistor 110 protect the input of a D Flip-Flop 112 from damage. The flip-flop 112 may be a typical CMOS HC74 device. The output of the flip-flop 112 transitions from a low to a high. The high signal level from the output of the flip-flop enables the output of an AND gate 114 to copy a 3.41 Hz precision clock signal, received from a second clock generator 115, to its output and through a NOR gate 116 to form an episode initiation signal on an episode signal line 118 in response to the output of the AND gate 114 going to a high state concurrently with the output of the flip-flop 112 going high. The complement output of the flip-flop 112 on a signal line 120 operates to reset the counter 84, as the output from the complement terminal goes low. The episode initiation signal is coupled to an input of the computer 50 on the episode signal line 118 from FIG. 3 to FIG. 2. The computer 50 generates an EPISODE signal to the ventilator on the ventilator actuation line 38 of FIGS. 1 and 2.

Figure 7:
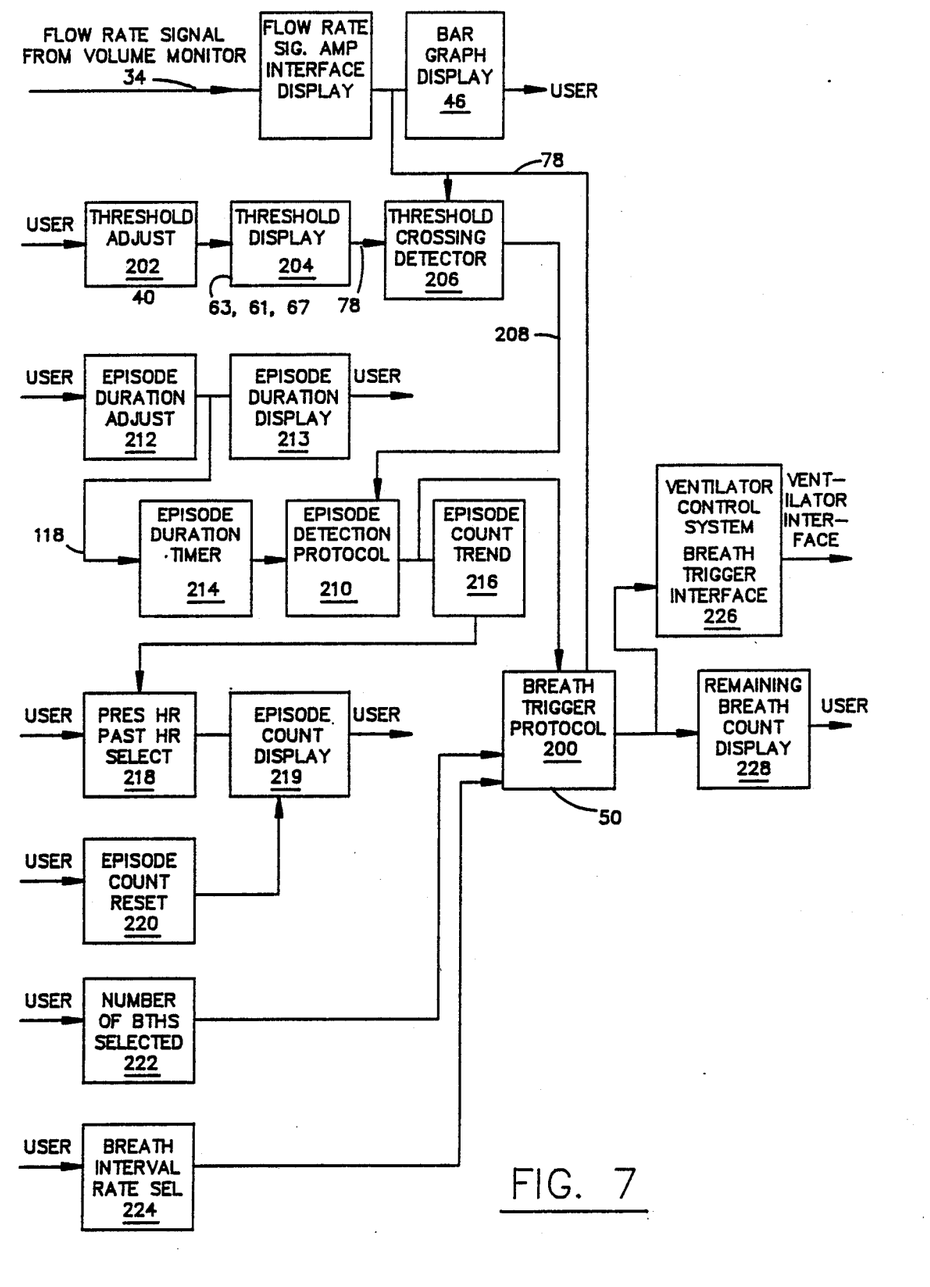
FIG. 7 is a simplified functional block diagram of the ventilator control system in accordance with the preferred embodiment.

FIG. 7 is a block diagram that characterizes the hardware/software architecture of the ventilator control system. The analog flow rate signal, such as waveform (b) of FIG. 5, is coupled from the volume monitor 34 to the flow rate signal amplifier 52, as shown in FIG. 2. The flow rate input signal is an analog signal, typically in the range of −5 to +5 volts, a signal range typically corresponding to an input flow rate range of −23.5 liters per minute to +23.5 liters per minute. The input signal is rectified by the diode 53 to obtain only positive excursions of the signal, thereby characterizing inspiration.

The bar graph display of FIGS. 1 and 2, shown as a block 46 in FIG. 7, is used to display the scaled positive values of the flow rate signal. The flow rate signal is coupled by the signal bus 78 to a breath trigger protocol 200, representing a program function within the computer 50.

A threshold adjust block 202 represents the process of providing a threshold signal from the threshold adjustment control 40 to a threshold display block 204 representing a selected LED on the bar graph display 46. The flow rate signal indication is superimposed onto the threshold signal indication by time multiplexing the values of the two signals onto a single bar graph to display the instantaneous values of both the flow rate signal and the threshold signals on a cascaded pair of analog bar graph/dot LED displays, using drivers that are programmed in the bar mode for flow rate display and in the dot mode for threshold display, as previously described. The duty cycles of the dot/bar modes for the drivers are selected to be other than 50%, in order to get a higher brightness for the threshold display and a lower brightness for the flow rate.

The threshold signal value is time multiplexed by the bus 78 to a threshold crossing detector 206 representing a program function within the computer 50.

As the magnitude of the flow rate signal on the bus 78 exceeds the threshold signal, the threshold crossing detector function of the block 206 provides a crossing signal via a signal line 208 to an episode detection protocol function, represented by a block 210.

A function block 212 characterizes the step in which the operator adjusts the duration adjustment control 42, shown in FIG. 1, to set the interval within which the positive flow rate signal must cross the operator selected threshold signal breath.

An episode duration timer function block 214 represents the function provided by operation of the binary counter 84, the DAC 90, the scaling amplifier 94 and the comparator circuit 98 of FIG. 3, as described above. The digital/analog timing circuit thus described is consistent with typical rate and inspiratory time controls on ventilators with which the ventilator control device may be used. Each valid threshold crossing clears the counter as discussed in connection with FIG. 3. As the timer times out (after a no-breath or low-breath activity pause of between 5 and 25 seconds, set by the operator using the duration adjustment control 42), a hardware interrupt, via the signal line 118, initiates processing by the computer 50, within the episode detection protocol function block 210, leading to the generation of one or more actuator signals to the ventilator on the actuation line 38 of FIGS. 1 and 2.

The episode detection protocol block 210 starts with an episode time out and ends with a valid threshold crossing, as a result of a spontaneous or mechanical breath. A new duration time timeout occurring during this time frame will not be considered as a new episode and will not be counted. However, if the episode is longer than thirty seconds, it will be considered completed even in the absence of a valid threshold crossing. Imposing this requirement eliminates the possibility of hardware/software hang-up. An episode interrupt software routine is implemented in the computer 50 to provide this function. The real time clock is addressed by the software to update the software routine to count the 30 seconds.

An episode count trend block 216 is a software count routine within the computer program that counts the events that occurred during the last two hours after the unit was powered-On or the episode counter was reset. The complexity of this function requires a trending software implementation that includes the following steps:

1. The episode count occurred in every minute is stored in a buffer.
2. The minute intervals are generated in the real-time clock interrupt.
3. The circular buffer length is 120 bytes (2 hours capacity).
4. The buffer has two sliding outpointers, advancing each minute.
5. The 0-60 minutes pointer starts at location 61.
6. The 61-120 minutes pointer starts at the beginning of the buffer.
7. The pointers are individually wrapped around after 120 minutes.
8. The counts are totalized to yield the total count desired, starting with the actual position of the desired pointer.
9. The operator selects the 0-60 or 61-120 minutes totalizing frame.
10. The desired count is displayed.

A present hour/past hour select function block 218 represents the step of using a momentary action pushbutton switch to select either a 0-60 or a 61-120 minutes totalizing frame. Appropriate markings (not shown) on the control panel 36 identify which frame is selected by the operator.

An episode count display block 219 represents the use of two seven segment indicators in the panel display 44 (FIG. 1), to display the present hour or past hour totalized count of episodes. An episode count reset block 220 represents the function of resetting the counters and the display.

A breath number selection function switch 222 represents the use of the 16 position rotary switch 48 on the panel 36 to provide binary coded decimal signals to the computer 50 to indicate that from one to four breaths are required after initiation of each episode. A software routine loads the switch setting into a counter that is decremented after each breath triggering signal. When the counter value reaches zero, the generation of breath triggering signals is stopped, and the counter is reloaded with the value commanded by the switch.

A breath interval selection block 224 provides for rotary switch selection of breath intervals of two, four, six, eight, and ten seconds (30, 15, 10, 7.5, and 6 breaths per minute), using the same 16 position switch 48 as in the function 222. A computer program routine loads the selected value into a counter that is decremented by the real time interrupt service routine.

The breath trigger protocol block 200 represents a subroutine that permits only one breath in the MPTB/IMV mode and the full programmed number of breaths from the position of the 16 position rotary switch 48 in the MPTB/CPAP mode. The MPTB/IMV single breath and the first breath in the MPTB/CPAP breath series are delivered only when there is no valid spontaneous breath initiated by the patient within the selected episode interval. The software routine determines the mode of the ventilator control system, and the number of breaths from the 16. position rotary switch 48. The routine delays the delivery of a first breath if the flow signal shows spontaneous patient activity. The routine provides the first MPTB breath delivery directly in the flow interrupt routine in order to synchronize with the patient's spontaneous respiration. The other breaths are less critical, so they are implemented in the main loop, reducing the interrupt overhead.

A ventilator control system breath trigger interface function 226 uses a frequency modulated duplex link to exchange information between the ventilator and the control system. The information to be exchanged is coded as a subset of the available 16 DTMF telephone audio frequency tone pairs using a DTMF transceiver such as the Silicon Systems 20C89, as described more fully below. The use of transceivers assures high noise immunity between the control system and the ventilator.

A remaining breath count display function block 228 represents a routine for driving the dual seven segment indicator 44 for approximately 2 seconds after each delivered breath with the count of the remaining breaths. The software uses the real time interrupt to monitor the countdown display time. The object of limiting the display time is to minimize interference with the display of the episode count in the same indicator.

Appendix A submitted herewith is a source code listing of an exemplary computer program that can be used to program the computer 50 to perform the above-described functions.

Figure 9:
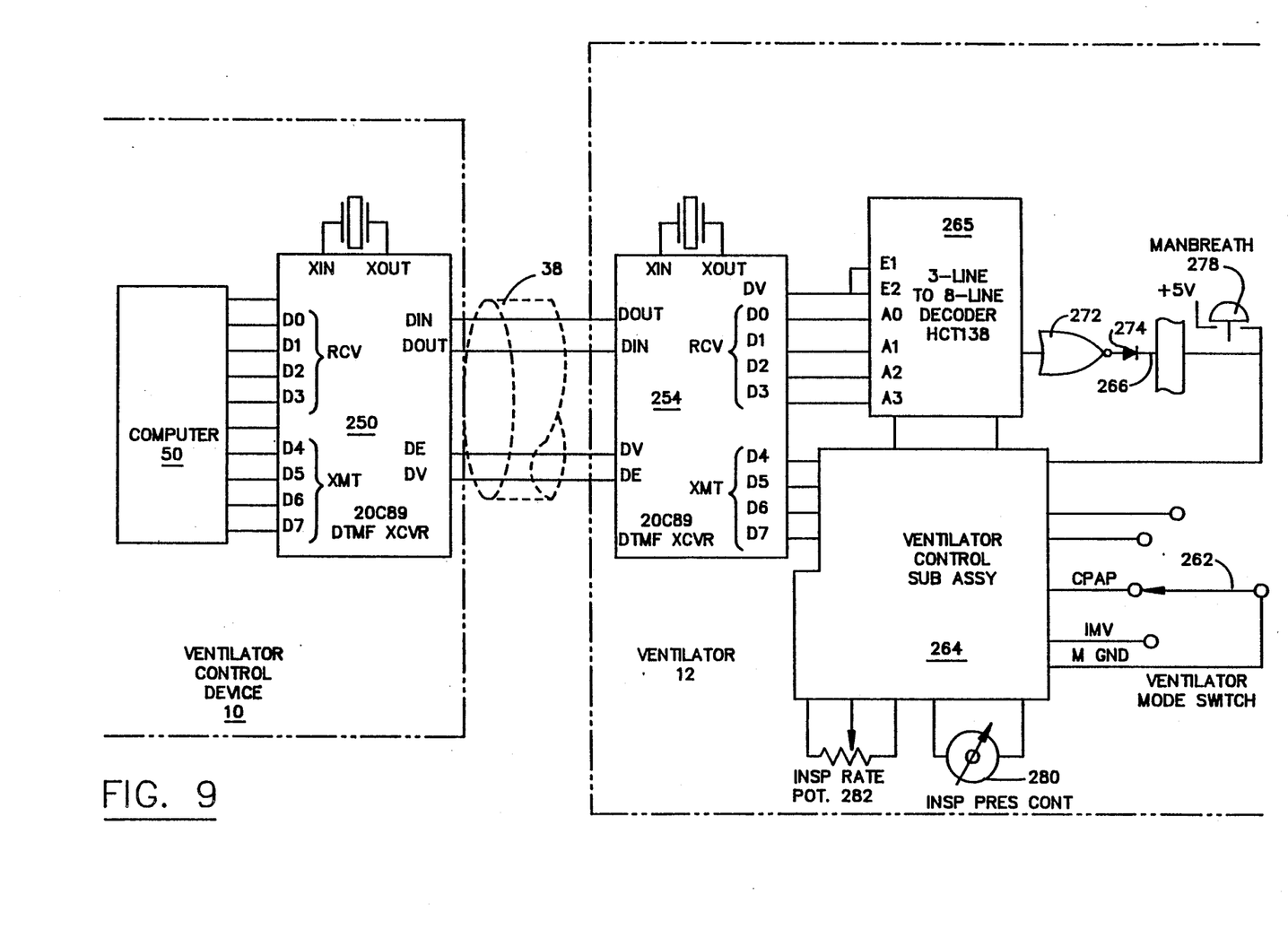
FIG. 9 is a schematic diagram of the circuitry within the ventilator that responds to the episode signal.

FIG. 9 shows the ventilator control device 10 linked to the ventilator 12 by the actuation line 38. Status information and commands, such as an episode signal, are transmitted from a first transceiver 250 on the DOUT line to a second DTMF transceiver 254 in the ventilator 12. Conversely, information is communicated from the second transceiver 254 on the DOUT signal line to the first transceiver 250 in the ventilator control device 10. The computer 50 provides information to be communicated to the first DTMF transceiver 250 via a conventional digital bus (not shown) within the ventilator control device 10.

The transceivers 250 and 254 have a receive bus designated as terminals D0-D3 and a transmit bus designated as D4-D7. Information to be transmitted is sent to the D0-D3 bus. One of sixteen tones is selected based on the state of the signals on the D0-D3 bus Conversely, the DTMF transceivers receive a tone and determine which of the 16 tones is being received. Once the DTMF device determines what tone is received, it prepares the four bit word to be communicated on the D4-D7 lines. The DE and DV signal lines are protocol lines for the purpose of indicating that a DTMF device is ready to read or ready to send.

The computer 50 interrogates the status of the ventilator on a continuing basis for the purpose of determining if the ventilator is operating in an error free mode. The computer makes it possible to continually monitor a large number of factors to determine if the ventilator is responsive to the computers commands. Alarms are sounded to alert the operator to error conditions.

When the operator positions the mode switch 49, shown in FIG. 1, to the MPTB position, the system comprising the ventilator and the control device 10 will operate either in the MPTB/CPAP mode or the MPTB/IMV mode depending on the position of a ventilator mode switch 262 shown in FIG. 9. The ventilator mode switch 262 commands a ventilator control subassembly 264 to operate in either the CPAP mode, the IMV mode or the STANDBY mode.

In the MPTB/CPAP mode, the control device 10 responds to the detection of an episode by sending the number of breath signals to the ventilator 12 as the operator designates with the breath count and interval switch 48. If the ventilator 12 is in the IMV mode, the ventilator control device 10 sends one breath signal to the ventilator for each episode that is detected.

The mode and control signals from the second DTMF transceiver 254 are processed by a "3-line to 8-line" decoder 265 for distribution to the ventilator control subassembly 264 on a signal line 266 after inversion by an inverter 272. A diode 274 provides protection for the DTMF circuitry. The signal line 266 carries the episode signals to the ventilator control subassembly 264 The episode signals on the signal line 266 are free to command as many ventilator breath cycles as are required by the ventilator control device 10. A switch 278 is a manual command switch, on the typical ventilator, that is customarily used to obtain a single breath.

It should be appreciated that the ventilator control device 10 is shown as a separate unit from the ventilator, so that existing ventilators can be modified to operate with the ventilator control device 10. The ventilator control device 10 is also capable of being incorporated into the design of a ventilator, thereby implementing the two way communications link provided by the transceivers 250 and 254.

Referring again to FIG. 9, a number of controls, such as an inspiration pressure control 280 and an inspiration rate potentiometer 282, control the performance characteristics of a typical ventilator capable of being modified to operate with the ventilator control device 10.

The inspiration pressure control 280 limits the amount of pressure that the patient is subjected to. The inspiration rate potentiometer 282 limits the cycle rate of the ventilator when operating in a timed or cyclic mode without the benefit of the ventilator control device 10.

Figure 8:
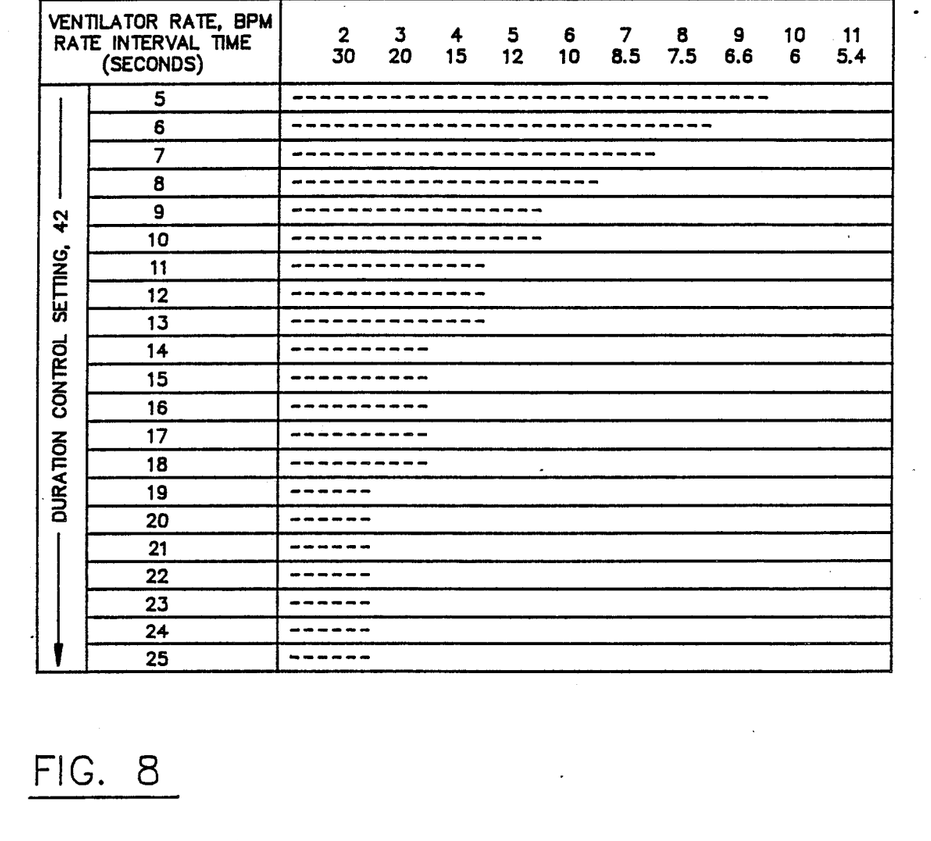
FIG. 8 is a Weaning Chart showing the relationship between breaths per minute and the time that the operator must select on the duration control to permit the ventilator control system to wean a patient back to normal breathing.

FIG. 8 relates the cyclic ventilator rate, established by adjusting the inspiration rate potentiometer 282 in FIG. 9, to the duration time that the operator sets on the duration control 42 shown in FIG. 1. The chart of FIG. 8 indicates that if the ventilator control device 10 is in the MPTB/IMV mode, the duration time must be set to a time value lower than the ventilator inspiration rate time interval. When the duration time for an episode is set for a longer interval than the ventilator breath rate interval time, the ventilator control device 10 cannot detect episodes. In the absence of a voluntary patient breath, the ventilator will deliver a mandatory breath before the duration interval of duration control 42 is expired. To wean a patient from a dependence on assistance from the ventilator, the ventilator rate is set to be an interval that is anticipated to be longer than the normal interval for breathing. The duration time is set to be a slightly shorter interval, but is also slightly longer than the expected interval between normal breaths.

For example, with a ventilator breath rate interval set to 7.5 seconds, FIG. 8 suggests that the duration time be set to less than 6.0 seconds to permit the ventilator control device 10 to be able to detect an episode.

What is claimed is:

1. A method of controlling a time-cycled constant-flow, pressure-limited medical ventilator during the ventilation of a patient, wherein the ventilator has a selectable breath rate interval, the method comprising the steps of:
    (a) sensing the inspiratory flow rate of the patient and generating a flow rate signal;
    (b) selecting a flow rate threshold value;
    (c) selecting an episode time interval;
    (d) selecting a number of ventilator-delivered breaths;
    (e) comparing the flow rate signal value to the selected flow rate threshold value during the selected episode time; and
    (f) actuating the ventilator to deliver the selected number of ventilator-delivered breaths to the patient if the flow rate signal value remains below the selected flow rate threshold value throughout the duration of the selected episode time interval.

2. The method of claim 1, wherein the actuation step comprises the steps of:
    (1) generating a breath indicative signal whenever the value of the flow rate signal equals or exceeds the selected flow rate threshold value;
    (2) interrupting and restarting the selected episode time interval in response to the breath-indicative signal; and
    (3) generating a ventilator actuation signal when the selected episode time interval elapses without interruption.

3. The method of claim 1, further comprising the step of:
    selecting the interval between the ventilator-delivered breaths to be delivered by the ventilator during the actuation step when the selected number of ventilator-delivered breaths is more than one.

4. The method of claim 1, wherein the ventilator has an intermittent mandatory ventilation mode, and wherein the actuation step comprises actuating the ventilator to deliver only one breath when the ventilator is in the intermittent mandatory ventilation mode, regardless of the number of ventilator-delivered breaths selected in the step of selecting the number of ventilator-delivered breaths.

5. A respiratory ventilator system for controllably ventilating a patient, wherein the system includes a time-cycled, constant-flow, pressure-limited ventilator operable in a mandatory ventilation mode with a selectable breath rate interval, and in a CPAP mode, the ventilator having an inspiratory flow line, an expiratory flow line, and a patient connector for coupling the inspiratory and expiratory flow lines to a patient, wherein the improvement comprises:

flow rate sensing means, in the patient connector, for generating a flow rate signal indicative of the flow rate of gas inspired by the patient through the connector; and a ventilator control device, receptive to the flow rate signal and operatively coupled to the ventilator, the ventilator control device comprising:

first control means for providing a selectable duration signal scaled to define a selected time interval;

second control means for providing a selectable flow rate threshold signal;

episode signal generation means, responsive to the flow rate signal, the duration signal, and the flow rate threshold signal, for generating an episode signal in response to the failure of the flow rate signal to attain the value of the flow rate threshold signal within the selected time interval; and ventilator actuation means, responsive to the episode signal, for actuating the ventilator to deliver a breath to the patient each time the episode signal is generated, independently of the selected breath rate interval of the ventilator, when the selected time interval is shorter than the selected breath rate interval of the ventilator operated in the mandatory ventilation mode.

6. The ventilator system of claim 5, wherein the episode signal generation means comprises:

computer means, responsive to the flow rate signal and to the flow rate threshold signal, for providing a breath-indicative signal each time the flow rate signal amplitude exceeds the flow rate threshold signal amplitude.

7. The ventilator system of claim 5 wherein said episode signal generation means further comprises:

computer means, responsive to the flow rate signal, to the flow rate threshold signal, and to the duration signal, for providing a breath-indicative signal each time the flow rate signal amplitude exceeds the flow rate threshold signal within the selected time interval.

8. The ventilator system of claim 5 wherein said episode signal generation means further comprises:

flow rate signal amplifier means, responsive to the flow rate signal, for amplifying the flow rate signal to provide an amplified flow rate signal.

9. The ventilator control system of claim 8, wherein said episode signal generation means further comprises:

flow rate threshold signal amplifier means, responsive to the flow rate threshold signal, for amplifying the flow rate threshold signal to provide an amplified flow rate threshold signal.

10. The ventilator system of claim 5, further comprising flow rate indicator means, and wherein the episode signal generation means further comprises:

driver means, responsive to the flow rate signal, for actuating the flow rate indicator means.

11. The ventilator system of claim 5, further comprising:

indicator means, responsive to the flow rate signal and to the flow rate threshold signal, for simultaneously indicating the value of the flow rate signal and the flow rate threshold signal.

12. The ventilator control system of claim 5, wherein the episode signal generation means further comprises:

driver means, responsive to the flow rate signal and to the flow rate threshold signal, for providing a weighted flow rate signal and a weighted flow rate threshold signal; and computer means, responsive to the weighted flow rate and weighted flow rate threshold signals, for providing a breath-indicative signal each have the weighted flow rate signal exceeds the weighted flow rate threshold signal.

13. The ventilator system of claim 5, further comprising:

third control means for generating a selectable ventilator breath signal indicative of a selected number of ventilator-delivered breaths;

wherein the ventilator actuation means is responsive to the episode signal and the ventilator breath signal for actuating the ventilator, when operated in the CPAP mode, to deliver the selected number of breaths to the patient each time the episode signal is generated.

14. The ventilator system of claim 13, wherein the third control means includes means for selectably varying the time interval between ventilator-delivered breaths if the selected number of ventilator-delivered breaths is at least two.

15. A respiratory ventilator system for controllably ventilating a patient, wherein the system includes a time-cycled, constant-flow, pressure-limited ventilator operable in a mandatory ventilation mode with a selectable breath rate interval, and in a CPAP mode, the ventilator having an inspiratory flow line, an expiratory flow line, and a patient connector for coupling the inspiratory and expiratory flow lines to a patient, wherein the improvement comprises:

first means for fluidly coupling the ventilator to a patient;

second means in the first means for sensing an inspiratory effort by the patient and generating a flow rate signal in response thereto; and a ventilator control device, operatively coupled to the ventilator, the ventilator control device comprising:

third means for providing a threshold signal having a selectable value;

fourth means for providing a selectable episode time interval;

fifth means for providing a selectable number of ventilator-delivered breaths when the ventilator is operated in the CPAP mode;

sixth means responsive to the flow rate signal and the threshold signal, for generating an episode signal when the value of the flow rate signal remains below the selected threshold signal value for the duration of the selected episode time interval; and seventh means for actuating the ventilator, when operated in the CPAP mode, to deliver the selected number of ventilator-delivered breaths in response to each episode signal.

16. The ventilator system of claim 15, further comprising:

eighth means, responsive to the flow rate signal and the threshold signal, for generating a breath-indicative signal whenever the the value of the flow rate signal equals or exceeds the value of the threshold signal; and ninth means, responsive to the breath indicative signal, for restarting the episode time interval in response to the breath-indicative signal.

17. The ventilator system of claim 16, further comprising:
   tenth means for providing a selectable episode count time span;
   eleventh means, responsive to the episode signal, for counting the number of times that the episode signal has been generated within the selected episode count time span to provide an episode count; and
   twelfth means, responsive to the eleventh means, for indicating the episode count.

18. The respiratory ventilator system of claim 15, wherein the ventilator actuation means is responsive to the episode signal for actuating the ventilator to deliver a breath to the patient each time the episode signal is generated independently of the selected breath rate interval of the ventilator, when the ventilator is operated in the mandatory ventilation mode, and when the selected episode time interval is shorter than the selected breath rate interval of the ventilator.

* * * * *

UNITED STATES PATENT AND TRADEMARK OFFICE
CERTIFICATE OF CORRECTION

PATENT NO. : 5,107,831

DATED : April 28, 1992

INVENTOR(S) : Arieh S. Halpern and Ioan T. Oltean

It is certified that error appears in the above-identified patent and that said Letters Patent is hereby corrected as shown below:

Column 1, line 45, "patient,s" should be --patient's--;

Column 2, line 45, "patient,s" should be --patient's--;

Column 4, line 57, "patient,s" should be --patient's--;

Column 7, line 15, after "the" insert --reset signal into binary counter input terminal 86, the counter-- in that it was inadvertently omitted.

Column 8, line 57, after "signal" insert --from the threshold adjustment control 40 to qualify as a valid-- in that it was inadvertently omitted;

Column 10, line 66, after "bus" insert --.--;

Column 11, line 36, after "264" insert --.--;

Column 12, line 30 (Claim 1), after "time" insert --interval-

Column 13, line 50 (Claim 9) after "ventilator" delete --control--;

Column 13, line 67 (Claim 12) after "ventilator" delete --control--; and

UNITED STATES PATENT AND TRADEMARK OFFICE
CERTIFICATE OF CORRECTION

PATENT NO. : 5,107,831

DATED : April 28, 1992

INVENTOR(S) : Arieh S. Halpern and Ioan T. Oltean

It is certified that error appears in the above-identified patent and that said Letters Patent is hereby corrected as shown below:

Column 14, line 7 (Claim 13) change "have" to --time--.

Signed and Sealed this

Tenth Day of August, 1993

Attest:

MICHAEL K. KIRK

*Attesting Officer*    Acting Commissioner of Patents and Trademarks